(12) United States Patent
Yoon (10) Patent No.: US 10,376,643 B2
(45) Date of Patent: Aug. 13, 2019

(54) INJECTION APPARATUS AND INJECTION METHOD USING SAME

(71) Applicant: PANACE CO., LTD., Seongnam-si, Gyeonggi-do (KR)

(72) Inventor: Sung Tae Yoon, Seoul (KR)

(73) Assignee: PANACE CO., LTD., Seongnam-si, Gyeonggi-Do (KR)

( * ) Notice: Subject to any disclaimer, the term of this patent is extended or adjusted under 35 U.S.C. 154(b) by 365 days.

(21) Appl. No.: 15/115,961

(22) PCT Filed: Dec. 23, 2014

(86) PCT No.: PCT/KR2014/012736
§ 371 (c)(1),
(2) Date: Aug. 2, 2016

(87) PCT Pub. No.: WO2015/119376
PCT Pub. Date: Aug. 13, 2015

(65) Prior Publication Data
US 2017/0157327 A1 Jun. 8, 2017

(30) Foreign Application Priority Data

Feb. 7, 2014 (KR) ........................ 10-2014-0014405

(51) Int. Cl.
*A61M 5/20* (2006.01)
*A61M 5/32* (2006.01)
*A61M 5/42* (2006.01)

(52) U.S. Cl.
CPC ............ *A61M 5/2053* (2013.01); *A61M 5/20* (2013.01); *A61M 5/3298* (2013.01); *A61M 5/425* (2013.01); *A61M 2205/3344* (2013.01)

(58) Field of Classification Search
CPC .. A61M 5/2053; A61M 5/3298; A61M 5/425; A61M 2205/3344
See application file for complete search history.

(56) References Cited

U.S. PATENT DOCUMENTS

2002/0016567 A1* 2/2002 Hochman ........... A61M 5/1456
604/131
2005/0131332 A1* 6/2005 Kelly .................. A61M 1/1696
604/4.01

FOREIGN PATENT DOCUMENTS

JP 2002-511317 A 4/2002
KR 10-2010-0136245 A 12/2010
(Continued)

*Primary Examiner* — Lauren P Farrar
(74) *Attorney, Agent, or Firm* — Rabin & Berdo, P.C.

(57) ABSTRACT

The present invention uses an injection apparatus comprising: an injector which includes a mounting part on which a syringe is mounted, a needle assembly having a plurality of needles, a motor and a screw for actuating a piston of the syringe forward and backward; and a main body for controlling the forward and backward actuation of the piston of the syringe and drug injection. The present invention is configured as follows: a vacuum suction pressure is formed in the needle assembly that is in contact with the skin; injection is performed so that a drug is injected through a needle after it is determined that the needle is in close contact with the skin by comparing a sensed vacuum suction pressure value with a preset vacuum suction pressure value; and if injection is completed, the needle assembly is separated from the skin.

15 Claims, 5 Drawing Sheets

(56) References Cited

FOREIGN PATENT DOCUMENTS

| | | |
|---|---|---|
| KR | 10-2012-0044612 A | 5/2012 |
| KR | 10-2013-0122209 A | 11/2013 |
| KR | 10-2013-0128788 A | 11/2013 |
| KR | 10-2013-0143280 A | 12/2013 |

* cited by examiner

INJECTION APPARATUS AND INJECTION METHOD USING SAME

TECHNICAL FIELD

The present disclosure relates to an injection apparatus including an injector, and an injection method using the same, and more particularly, to an injection method and an injection apparatus according to which, when the injection apparatus is turned on and a needle assembly is brought into contact with skin, drug injection is performed by the vacuum suction pressure, and after a predetermined dosage of drug is injected, further injection of the drug is blocked such that loss of drug is prevented, and the injection apparatus senses the vacuum suction pressure and provides an injection automatically, i.e., without requiring a practitioner's separate operation.

BACKGROUND ART

Syringes are widely used to inject drugs into a human body. Korean Patent No. 10-2010-0136245 discloses "Automatic injection gun". Further, Korean Patent No. 10-2012-0044612 discloses "Skin treatment module". However, the related art requires the practitioner to repeat the process of inserting a needle, operating a switch to inject the drug, and removing the needles several times, thus rapidly increasing the practitioner's fatigue as the treatment continues. Further, the injection apparatus that automatically injects drug causes a considerable amount of drug loss when the practitioner has a low proficiency level.

DISCLOSURE OF INVENTION

Technical Problem

The present disclosure has been made to overcome the problems occurring in the art, and accordingly, it is an object of the present disclosure to provide an injection method and an injection apparatus according to which needles are inserted into skin when a needle assembly is brought into a close contact with the skin by vacuum suction pressure and a predetermined dosage of drug is injected, and the suction pressure is released after the predetermined dosage of drug is injected into the skin and the needle assembly is separated apart from the skin such that the injection apparatus senses the vacuum suction pressure and automatically provides an injection without requiring a separate operation of a practitioner.

Solution to Problem

The above and other objectives of the present disclosure are accomplished by an injection apparatus including an injector including a mounting part on which a syringe is mounted, a needle assembly provided with a plurality of needles, a motor and a screw that actuate a piston of the syringe forward and backward, and a main body that controls the forward and backward actuation of the piston of the syringe and drug injection.

The main body includes a main board 510 connected to the motor to provide an electrical signal to thus control the drug injection of the needles 121; an air hose 520 connected with one end to the needle assembly 120 and connected with the other end to a fitting 521 provided on the main body 500; a first suction pipe 541 provided in the main body 500 and connected with one end to the fitting 521 to be communicated with the air hose 520 and connected with the other end to an air filter 530; the air filter 530 provided in the main body 500 and connected with one end to the first suction pipe 541 and connected with the other end to the second suction pipe 542 to filter the air sucked in from the air hose 520; a four-directional connector 550 including first to fourth connectors 551-554 formed thereon wherein the second suction pipe 542 is connected to the first connector 551, the third suction pipe 543 connected to a suction pressure sensor 560 is connected to the second connector 552, the fourth suction pipe 544 connected to a suction motor 580 is connected to the third connector 553, and the fifth suction pipe 545 connected to a solenoid valve 570 is connected to the fourth connector 554; the suction pressure sensor 560 formed on the main board 510 and connected to the second connector (552) to sense the suction pressure at the four-directional connector 550; the suction motor 580 connected to the fourth suction pipe 544 to generate suction pressure to suck in air from the air filter 530; the solenoid valve 570 connected to the fifth suction pipe 545 to control opening and closing; a microcomputer formed on the main board 510 to compare a suction sense pressure transmitted from the suction pressure sensor 560 with a preset suction pressure to thus sense insertion of the needles 121 into the skin, and control the operation of the motor of the injector 100 to inject a preset dosage of drug through the needle 121; a power switch 610 that controls on and off of the injection apparatus; and a power supply 700 that supplies power to the injection apparatus.

The injection apparatus includes a foot switch connected to the main board to control drug injection manually.

The injection apparatus includes a drain pipe D connected to the suction motor 580 and opened in accordance with an operation of the solenoid valve 570 to discharge a liquid sucked into the air hose 520.

Meanwhile, an injection method using the injection apparatus having the injector as set forth above is provided, which may include a first step (S1) of setting one or more of drug injection mode, suction pressure, and a dosage of drug injection; a second step (S2) of bringing the front end of the needle assembly 120 of the injector 100 into contact with the skin such that the skin blocks the front end of the needle, suction pressure is generated through the first suction pipe 541 and vacuum suction pressure is generated at the needle assembly 120 in contact with the skin; a third step (S3) of comparing the vacuum suction pressure sensed at S2 with the preset suction pressure value to determine whether or not the needles 121 are inserted into the skin; a fourth step (S4) of driving the motor of the injector 100 and performing treatment of injecting the drug through the needle 121; and a fifth step (S5) of stopping the suction motor 680 upon completion of the drug injection, and opening the solenoid valve 570 to release the vacuum suction pressure such that the needle assembly 120 is separated apart from the skin.

The fifth step (S5) includes steps of releasing the suction pressure by turning off the power of the motor; and opening the solenoid valve, in which the opening of the solenoid valve allows external air to be introduced into the first suction pipe and the air hose, and to the injector, thus releasing the vacuum suction pressure and allowing the needle assembly to be separated apart from the skin.

The first step may additionally set an on/off interval of the suction motor.

Liquid sucked in through the needles by the on operation of the suction motor is discharged through the drain pipe D via the first suction pipe and the four-directional connector.

Advantageous Effects

According to the present disclosure, the injection apparatus is operated and the needle assembly is then brought into contact with the skin such that drug is injected by the vacuum suction pressure, and once the predetermined dosage of drug is injected, drug injection is blocked. Accordingly, drug can be injected without loss. Further, the injection apparatus does not require a practitioner to separately operate the injection apparatus for the purpose of drug injection, because the injection apparatus can sense the vacuum suction pressure and provide an injection automatically. Accordingly, fatigue of the practitioner is reduced. Further, an accurate dosage of drug can be injected, and because vacuum suction pressure is adjustable, possibility of bruised skin can be prevented.

BEST MODE FOR THE INVENTION

An injection apparatus according to an exemplary embodiment includes: an injector 100 including a mounting part on which a syringe is mounted, a needle assembly 120 including a plurality of needles, and a motor and a screw that actuate a piston of the syringe forward and backward; and a main body 500 that controls forward and backward actuation of the piston of the syringe and drug injection, in which the main body 500 includes a main board 510 connected to the motor to provide an electrical signal to thus control the drug injection of the needles 121; an air hose 520 connected with one end to the needle assembly 120 and connected with the other end to a fitting 521 provided on the main body 500; a first suction pipe 541 provided in the main body 500 and connected with one end to the fitting 521 to be communicated with the air hose 520 and connected with the other end to an air filter 530; the air filter 530 provided in the main body 500 and connected with one end to the first suction pipe 541 and connected with the other end to the second suction pipe 542 to filter the air sucked in from the air hose 520; a four-directional connector 550 including first to fourth connectors 551-554 formed thereon in which the second suction pipe 542 is connected to the first connector 551, the third suction pipe 543 connected to a suction pressure sensor 560 is connected to the second connector 552, the fourth suction pipe 544 connected to a suction motor 580 is connected to the third connector 553, and the fifth suction pipe 545 connected to a solenoid valve 570 is connected to the fourth connector 554; the suction pressure sensor 560 formed on the main board 510 and connected to the second connector (552) to sense the suction pressure at the four-directional connector 550; the suction motor 580 connected to the fourth suction pipe 544 to generate suction pressure to suck in air from the air filter 530; the solenoid valve 570 connected to the fifth suction pipe 545 to control opening and closing; a microcomputer formed on the main board 510 to compare a suction sense pressure transmitted from the suction pressure sensor 560 with a preset suction pressure to thus sense insertion of the needles 121 into the skin, and control the operation of the motor of the injector 100 to inject a preset dosage of drug through the needle 121; a power switch 610 that controls on and off of the injection apparatus; and a power supply 700 that supplies power to the injection apparatus.

Description of Embodiment

Hereinbelow, the preferred embodiments of the present disclosure are described in detail based on the drawings accompanied.

The embodiments described herein are provided to explain in detail to enable those skilled in the art to easily achieve the present disclosure, but not to be construed as limiting the technical concepts and scopes of the present disclosure.

Further, sizes or shapes of elements illustrated in the drawings may be exaggerated for the purpose of clarity and convenience of the description, and it is to be noted that certain terms that are specially defined in consideration of the configuration and operation of the present disclosure may vary depending on the intent of a user or an operator or by practices, and definitions of these terms will have to be made based on the explanation provided throughout the description.

Figure 1:
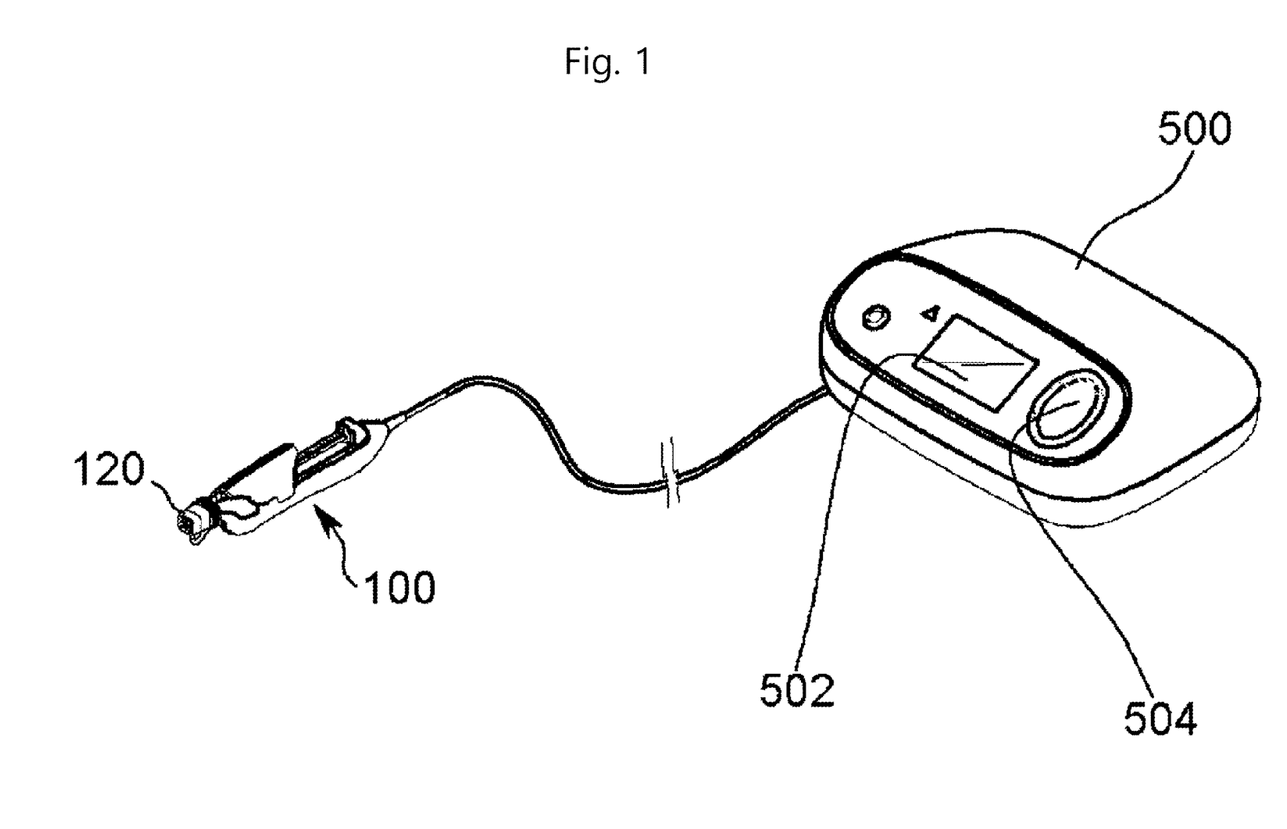
FIGS. 1 and 2 are perspective views of an injection apparatus according to an exemplary embodiment.
Figure 2:
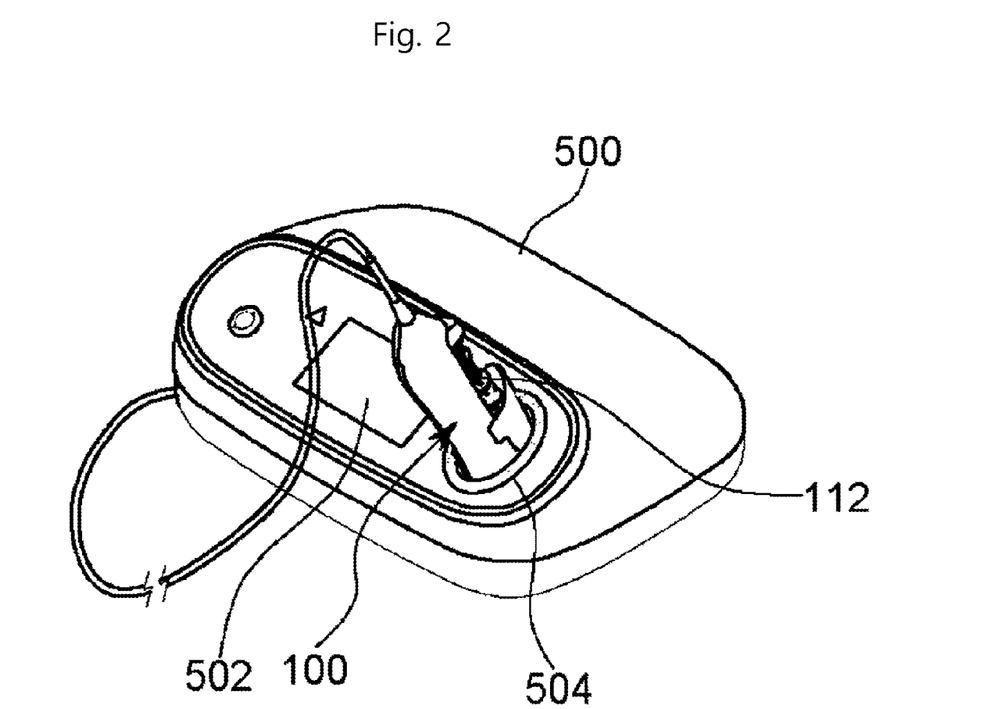
Figure 3:
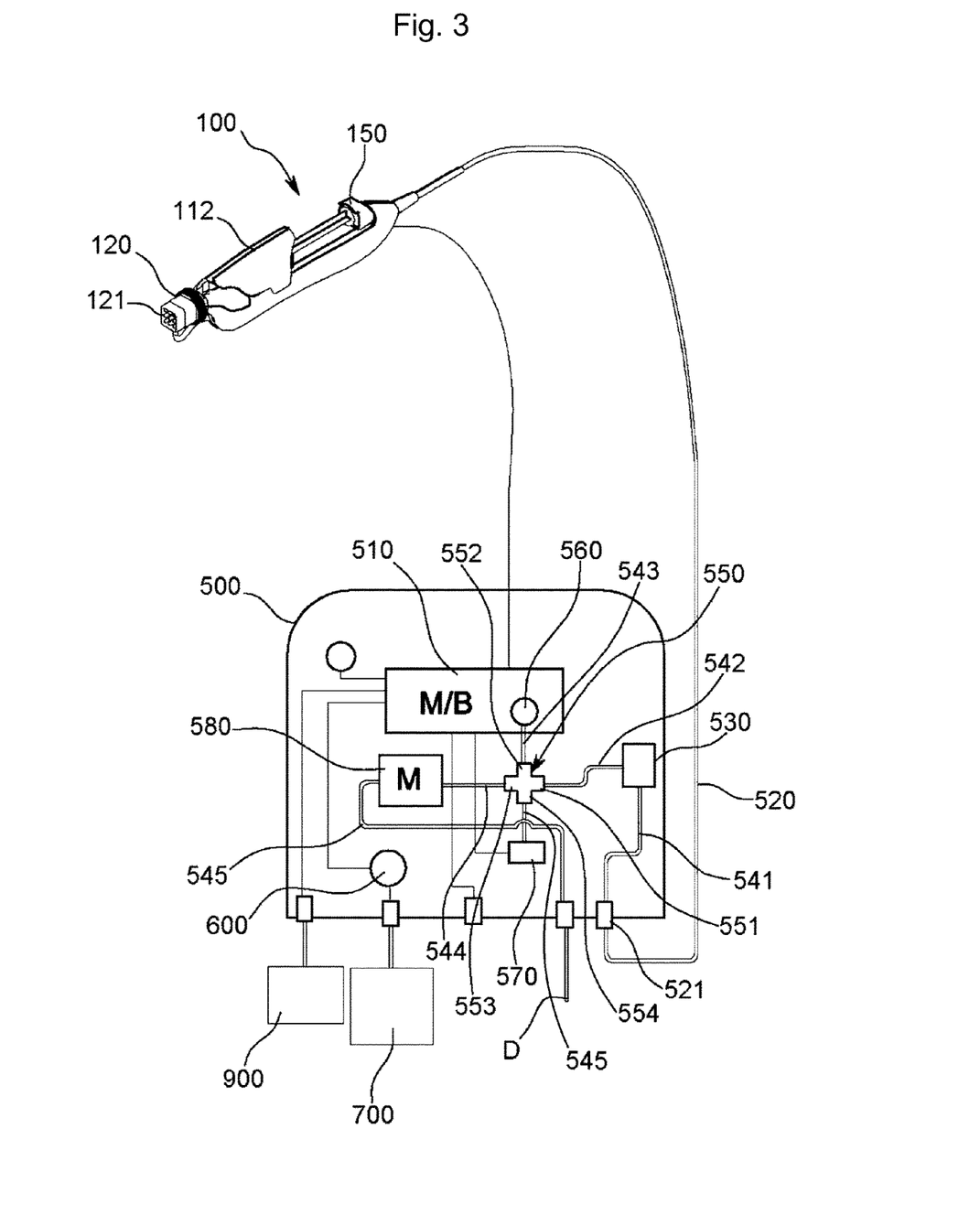
FIG. 3 shows a configuration of the injection apparatus illustrated in FIG. 1 according to an exemplary embodiment.
Figure 4:
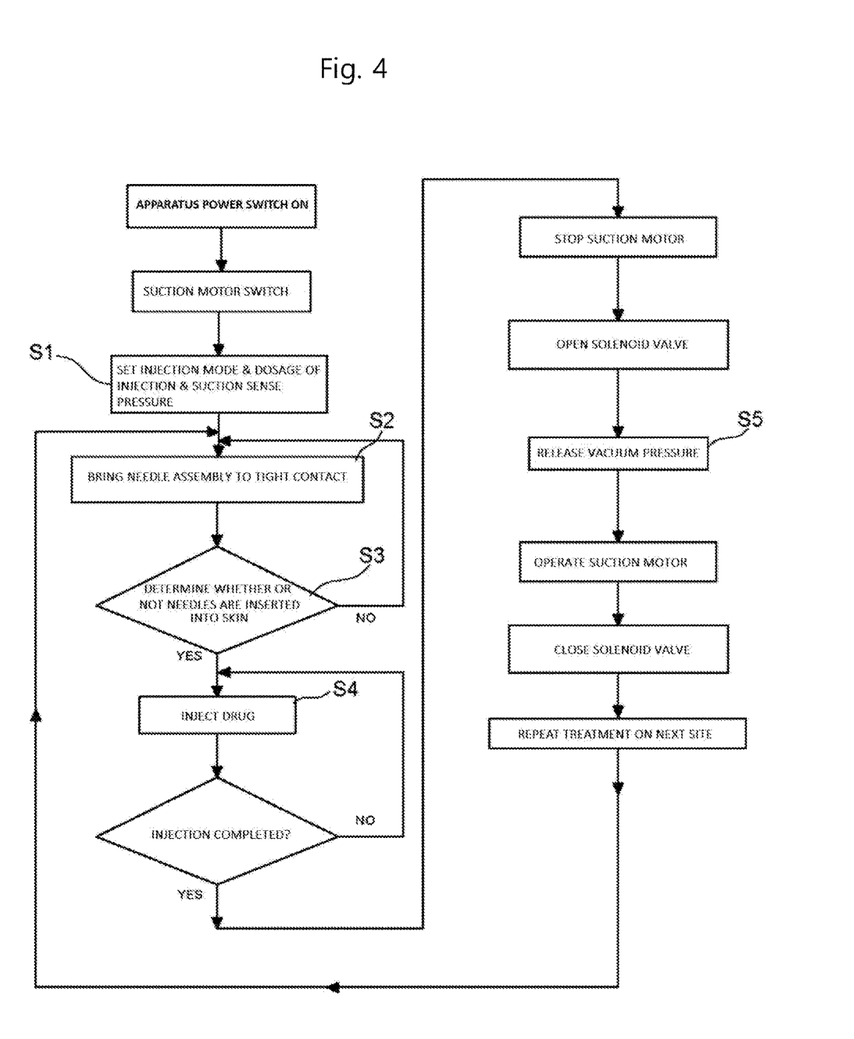
FIG. 4 is a flowchart provided to explain an injection method using an injection apparatus according to an exemplary embodiment.
Figure 5:
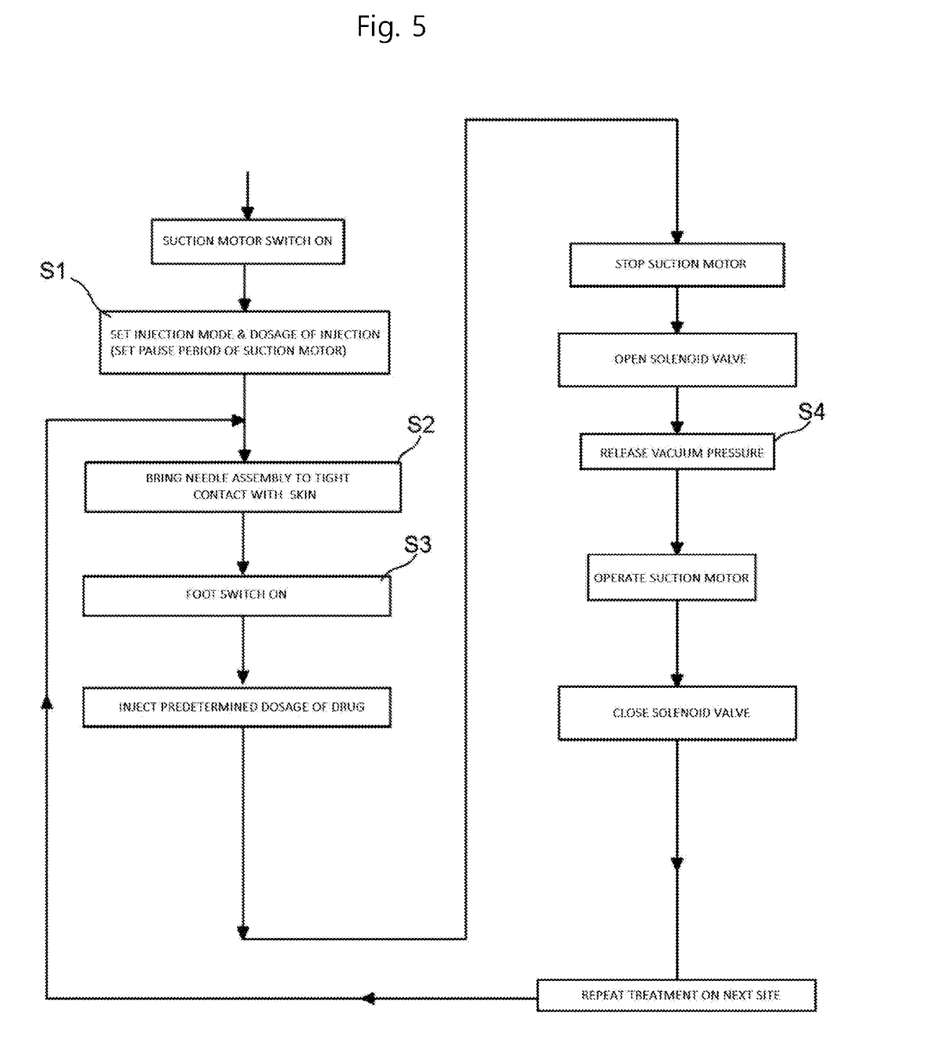
FIG. 5 is a flowchart provided to explain another injection method according to an exemplary embodiment.

FIGS. 1 and 2 are perspective views of an injection apparatus according to an exemplary embodiment, FIG. 3 shows a configuration of the injection apparatus illustrated in FIG. 1 according to an exemplary embodiment, and FIGS. 4 and 5 are flowcharts provided to explain an injection method using an injection apparatus according to an exemplary embodiment.

As illustrated in FIGS. 1 to 3, the injection apparatus according to the present disclosure includes an injector 100 including a mounting part 112 on which a syringe is mounted, a needle assembly 120 provided with a plurality of needles 121, a motor and a screw that actuate a piston of the syringe forward and backward; and a main body 500 that controls forward and backward actuation of the piston of the syringe and drug injection. The injector 100 is configured such that the mounting part mounted to press the piston of the syringe is formed on an upper portion, and a needle assembly 120 is mounted on a front portion, and includes therein a motor (not illustrated) to press the piston of the syringe and a screw (not illustrated) rotated in accordance with the motor, and an operating rod 150 engaged with the screw to push and press a rear end of the piston.

The motor is driven in response to a signal received from the main board 510.

The needle assembly 120 includes a hub 122 to which a plurality of needles 121 are coupled, and a case 123 to receive the hub 122 engaged therein. One side of the case 123 includes a connecting hole 124 connected to the syringe such that drug is fed from the syringe.

The hub 122 has a plurality of through-holes formed therein to be engaged with a plurality of needles 121, and the front surface of the hub 122 takes a planar form to facilitate tight contact against the skin.

The hub 122 and the case 123 are movably fastened with each other such that a length that the needles are exposed can be adjusted. The hub 122 and the case 123 may be fastened with screws.

The main body 500 includes a touch screen 502 on one side, and a holder 504 on the other side, on which the injector 100 is inserted and supported.

The main body 500 includes therein: a main board 510 connected to the motor to control drug injection of the needles 121 by providing an electrical signal; an air hose 520 connected with one end to the needle assembly 120 and connected with the other end to a fitting 521 provided on the main body 500; a first suction pipe 541 provided in the main body 500 and connected with one end to the fitting 521 to be communicated with the air hose 520 and connected with the other end to an air filter 530; the air filter 530 provided in the main body 500 and connected with one end to the first suction pipe 541 and connected with the other end to the second suction pipe 542 to filter the air sucked in from the air hose 520; a four-directional connector 550 including first to fourth connectors 551-554 formed thereon in which the second suction pipe 542 is connected to the first connector 551, the third suction pipe 543 connected to a suction pressure sensor 560 is connected to the second connector 552, the fourth suction pipe 544 connected to a suction motor 580 is connected to the third connector 553, and the fifth suction pipe 545 connected to a solenoid valve 570 is connected to the fourth connector 554; the suction pressure sensor 560 formed on the main board 510 and connected to the second connector (552) to sense the suction pressure at the four-directional connector 550; the suction motor 580 connected to the fourth suction pipe 544 to generate suction pressure to suck in air from the air filter 530; the solenoid valve 570 connected to the fifth suction pipe 545 to control opening and closing; a microcomputer formed on the main board 510 to compare a suction sense pressure transmitted from the suction pressure sensor 560 with a preset suction pressure to thus sense insertion of the needles 121 into the skin, and control the operation of the motor of the injector 100 to inject a preset dosage of drug through the needles 121; a power switch 610 that controls on and off of the injection apparatus; and a power supply 700 that supplies power to the injection apparatus.

A foot switch 900 is included, which is connected to the main board 510 and controls the manner of injection performed by the injector 100.

The foot switch 900 controls the operation to be selectively performed among: a continuous mode in which on/off operation of the motor of the injector 100 is maintained for a predetermined time period such that the drug injection continues for the predetermined time period; a dose mode in which short on/off operation of the motor of the injector 100 is repeated such that short drug injection repeats continuously; and a sensor mode in which the suction pressure value is perceived such that the injection is provided automatically.

A drain pipe D is included, which is connected to the suction motor 580 and opened by the operation of the solenoid valve 570 to discharge the liquid sucked into the air hose 520.

The treatment includes, first, operating the suction motor by turning on the power switch of the injection apparatus such that air is sucked into the needle assembly through the air hose.

Meanwhile, as illustrated in FIG. 4, the injection method using the injection apparatus described above includes: a first step (S1) of setting one or more of drug injection mode, suction pressure, and a dosage of drug injection; a second step (S2) of bringing the front end of the needle assembly 120 of the injector 100 into contact with the skin such that the skin blocks the front end of the needle, suction pressure is generated through the first suction pipe 541 and vacuum suction pressure is generated at the needle assembly 120 in contact with the skin; a third step (S3) of comparing the vacuum suction pressure sensed at S2 with the preset suction pressure value to determine whether or not the needles 121 are inserted into the skin; a fourth step (S4) of driving the motor of the injector 100 and performing treatment of injecting the drug through the needles 121; and a fifth step (S5) of turning off the motor power switch upon completion of the drug injection to thus stop the suction motor 580, and opening the solenoid valve 570 to release the vacuum suction pressure such that the needle assembly 120 is separated apart from the skin.

Prior to S1, a step of setting a length of exposure of the needles 121 according to the depth of insertion into the skin, is additionally included. The needle assembly 120 may be formed as a screw type to adjust the length of exposure of the needles. Accordingly, effective treatment is enabled, because it is possible to adjust the length of exposure of the needles to allow drug to be injected to the desired depth in the skin. The drug injection mode in S1 is selected among: the continuous mode in which a predetermined dosage of drug is continuously injected; a dose mode in which a small dosage of drug is repeatedly injected several times; and the sensor mode in which the suction pressure value is perceived for the injection. Further, the suction pressure can be set. That is, the suction pressure is set to be strong or weak, depending on the elasticity of the skin and thickness of the skin. The dosage of drug injection may be set according to a site for treatment, condition of a practitioner, and so on. The first step (S1) may additionally set the on/off interval of the suction motor 580. When the drug injection is provided once, the needle assembly 120 is separated apart from the skin such that the vacuum suction pressure is released. Then the suction motor 590 is operated again, the needle assembly 120 is brought into contact with the skin, the vacuum suction pressure is sensed, and the drug is injected into the skin. Then the suction motor 580 is stopped, the vacuum suction pressure is released, and the entire process described above repeats. In the process described above, the time interval at which the suction motor 580 is operated and stopped may be set. That is, the on/off interval may be set according to the level of proficiency of the practitioner such that the on/off interval may be set to be short for a skilled practitioner, while the longer on/off interval may be set for a less-skillful practitioner. Accordingly, convenience of treatment can be enhanced.

The second step (S2) involves grabbing the injector 100 and bringing the front surface of the hub 122 of the needles 121 into tight contact with the skin such that the vacuum suction pressure is generated. The vacuum suction pressure causes the skin to be attached tightly onto the front surface of the hub 122 of the needles 121 such that the needles 121 are inserted into the skin.

The third step (S3) involves determining whether or not the needles 121 are in tight contact with the skin, and whether or not the needles are inserted into the skin, by calculating the suction pressure (i.e., vacuum suction pressure) under which the skin is attached. When the needles are not inserted into the skin, the needle assembly 120 is brought into tight contact with the skin such that the needles are inserted. With the needles 121 being in contact with the skin, vacuum suction pressure is generated and the skin is sucked and the needles 121 are inserted into the skin. The air sucked from the air hose 520 is passed through the air filter 530 and introduced into the suction motor 580 via the four-directional connector 550. Because the third suction pipe 543 and the fifth suction pipe 545 are in closed state, vacuum state is formed only with the suction by the air hose 520 and the first and second suction pipes 541, 542.

The fourth step (S4) involves automatic treatment in which the motor of the injector 100 is driven to advance the piston of the syringe and inject the drug into the skin through the needles 121. The suction pressure sensor 560 sensing the vacuum suction pressure introduced through the air hose 520 as described above determines that the needles are inserted into the skin, and accordingly, the motor of the injector 100 is driven and the drug is injected into the skin through the needles 121. The drug is injected according to an initially-set injection dosage.

When the injection finishes, the fifth step (S5) stops the suction motor 580 and opens the solenoid valve 570 to release the suction pressure.

The treatment then continues on another site for treatment, by operating the suction motor 580, closing the solenoid valve 570 and bringing the needles 121 into tight contact with the skin.

Meanwhile, manual operation is possible. As illustrated in FIG. 5, a practitioner injects drug by manipulating the foot switch 900. The injection process may include a first step (S1) of setting one or more of drug injection mode, suction pressure, and dosage of drug injection; a second step (S2) of bringing the front end of the needle assembly 120 of the injector 100 into contact with the skin such that the skin blocks the front end of the needle assembly 120 and suction pressure is generated through the first suction pipe 541 and the vacuum suction pressure is formed at the needle assembly 120 in contact with the skin; a third step (S3) of driving a motor of the injector 100 with the foot switch 900 such that the drug is injected into the skin through the needles 121; and, upon completion of the drug injection, a fourth step (S4) of stopping the suction motor 580 and opening the solenoid valve 570 to release the suction pressure such that the needle assembly 120 is separated apart from the skin.

Prior to S1, a step of setting a length of exposure of the needles 121 according to the depth of insertion into the skin, is additionally included. The needle assembly 120 may be formed as a screw type to adjust the length of exposure of the needles. Accordingly, effective treatment is enabled because it is possible to adjust the length of exposure of the needles to allow drug to be injected to the desired depth in the skin. The drug injection mode in S1 is selected among the continuous mode in which a predetermined dosage of drug is continuously injected, or a dose mode in which a small dosage of drug is repeatedly injected several times. Further, the suction pressure can be set. That is, the suction pressure is set to be strong or weak, depending on the elasticity of the skin and thickness of the skin. The dosage of drug injection may be set according to a purpose of treatment, condition of a practitioner, and so on. The first step (S1) may additionally set the on/off interval of the suction motor 580. When the drug injection is provided once, the needle assembly 120 is separated apart from the skin such that the vacuum suction pressure is released. Then the suction motor 590 is operated again, the needle assembly 120 is brought into contact with the skin, the vacuum suction pressure is sensed, and the drug is injected into the skin. Then the suction motor 580 is stopped, the vacuum suction pressure is released, and the entire process described above repeats. In the process described above, the time interval at which the suction motor 580 is operated and stopped may be set. That is, the on/off interval may be set according to the level of proficiency of the practitioner such that the on/off interval may be set to be short for a skilled practitioner, while the longer on/off interval may be set for a less-skillful practitioner. Accordingly, convenience of treatment can be enhanced.

The second step (S2) brings the front end of the needle assembly 120 of the injector 100 to contact with the skin such that the suction pressure is generated through the first suction pipe 541 and vacuum suction pressure is formed at the needle assembly 120 in contact with the skin. The air sucked in through the air hose 520 is passed through the air filter 530 and introduced into the suction motor 580 via the four-directional connector 550. Because the third suction pipe 543 and the fifth suction pipe 545 are in closed state, the vacuum state is formed only with the suction by the air hose 520, and the first and second suction pipes 541, 542.

The third step (S3) involves the practitioner determining whether or not the needles 121 is in tight contact with the skin and whether or not the needles are inserted into the skin, and using the foot switch 900, driving the motor of the injector 100 such that the drug is injected into the skin through the needles 121. The third step (S3) selects among the continuous mode in which in accordance with continuous switching on of the foot switch 900, the motor of the injector 100 repeats operating on and off according to preset drug injection intervals such that drug injection continues for a predetermined time period, and a dose mode in which, in accordance with the switching on of the foot switch 900, the motor of the injector 100 is operated one time according to the preset drug injection intervals such that drug is injected every time the foot switch 900 is operated. The continuous mode and the dose mode may be selectively used in consideration of the site of treatment and the level of proficiency of the practitioner. For example, for the purpose of convenience, the dose mode may be used when it is necessary to inject a low dosage of drug in a denser pattern, while the continuous mode may be used when it is necessary to inject a high dosage of drug.

Once the injection of the predetermined dosage of drug is completed, the fourth step (S4) stops the suction motor 580 and releases the vacuum suction pressure such that the needle assembly 120 is separated apart from the skin. That is, the fourth step (S4) includes steps of releasing the suction pressure by turning off the power of the motor, and opening the solenoid valve 570, in which the opening of the solenoid valve 570 allows external air to be introduced into the first suction pipe 541 and the air hose 520, and to the injector 100, thus releasing the vacuum suction pressure and allowing the needle assembly 120 to be separated apart from the skin.

When the injection is completed, the foot switch 900 is turned off such that the suction motor 580 is stopped, and the solenoid valve 570 is opened such that the suction pressure is released.

The treatment then continues on another site for treatment, by turning on the foot switch 900 to operate the suction motor 580, and closing the solenoid valve 570 to bring the needles 121 into tight contact with the skin.

Meanwhile, a cleaning step is included to discharge liquid such as water or body fluid other than drug when such liquid is introduced into the suction passage including the air hose 520 and the suction motor 580. The cleaning step is performed with a precondition that the syringe is removed, by turning on the suction motor 580 according to which the water sucked in through the needles 121 is passed through the first suction pipe 541 and the four-directional connector 550, and discharged through the drain pipe 580.

The foregoing exemplary embodiments and advantages are merely exemplary and a variety of modifications may be enabled without departing from the technical scope of the present disclosure. Accordingly, the present teaching is not to be construed as limiting the exemplary embodiments. The present teaching is to be interpreted by the claims appended hereto, and all the technologies within the equivalent scope are to be interpreted as being included in the scope of the present disclosure.

INDUSTRIAL APPLICABILITY

The present disclosure relates to an injection apparatus that senses vacuum suction pressure and automatically provides injection, and is applicable in medical and cosmetic fields.

What is claimed is:

1. An injection apparatus, comprising:
    an injector (100) including a mounting part (112) on which a syringe is mounted, a needle assembly (120) provided with a plurality of needles, a motor and a screw that actuate a piston of the syringe forward and backward, the needle assembly (120) having a front rim configured to surround the plurality of needles and to come in contact with a skin of a patient; and
    a main body (500) that controls the forward and backward actuation of the piston of the syringe and drug injection,
    wherein the main body (500) comprises,
    a main board (510) connected to the motor to provide an electrical signal to thus control the drug injection of the needles (121);
    an air hose (520) having one end connected to the needle assembly (120) and the other end connected to a fitting (521) provided on the main body (500);
    a first suction pipe (541) provided in the main body (500), the first suction pipe having (541) one end connected to the fitting (521) to be communicated with the air hose (520) and the other end connected to an air filter (530);
    the air filter (530) provided in the main body (500), the air filter (530) having one end connected to the first suction pipe (541) and the other end connected to the second suction pipe (542) to filter the air sucked in from the air hose (520);
    a four-directional connector (550) including first to fourth connectors (551-554) formed thereon wherein the second suction pipe (542) is connected to the first connector (551);
    a third suction pipe (543) connected to the second connector (552);
    a fourth suction pipe (544) connected to the third connector (553);
    a fifth suction pipe (545) connected to the fourth connector (554);
    a suction motor (580) connected to the fourth suction pipe (544), the suction motor generating suction pressure to suck in air from the air filter (530);
    a suction pressure sensor (560) formed on the main board (510) and connected to the second connector (552) via the third suction pipe (543) to sense the suction pressure at the four-directional connector (550);
    a solenoid valve (570) connected to the fifth suction pipe (545) to control opening and closing;
    a microcomputer formed on the main board (510) to compare the suction pressure sensed by and transmitted from the suction pressure sensor (560) with a preset suction pressure to thus sense insertion of the needles (121) into the skin, and control operation of the motor of the injector (100) to inject a preset dosage of drug through the needles (121);
    a power switch (600) that controls on and off of the injection apparatus; and
    a power supply (700) that supplies power to the injection apparatus,
    wherein the front rim of the needle assembly (120) is configured to come in contact with and be blocked by the skin with the needles facing the skin, such that vacuum suction pressure is generated at the needle assembly (120) in contact with the skin, in accordance with operation of the suction motor (580) to suck in air from an internal space of the needle assembly (120) via the air hose (520), the first suction pipe (541), the air filter (530), the second suction pipe (542), the four-directional connector (550) and the fourth suction pipe (544), and the needles are inserted into the skin as the skin is drawn toward the needles by the vacuum suction pressure.

2. The injection apparatus of claim 1, comprising a foot switch (900) connected to the main board (510) to control drug injection manually.

3. An injection method using the injection apparatus as set forth in claim 2, the injection method comprising:
    a first step (S1) of setting one or more of drug injection mode, suction pressure, and dosage of drug injection;
    a second step (S2) of bringing the front rim of the needle assembly (120) of the injector (100) into contact with the skin such that the suction pressure is generated through the suction motor and the first suction pipe (541) and the vacuum suction pressure is formed at the needle assembly (120) in contact with the skin;
    a third step (S3) of driving the motor of the injector (100) with the foot switch (900) such that the drug is injected into the skin through the needles (121); and
    upon completion of the drug injection, a fourth step (S4) of stopping the suction motor (580) and opening the solenoid valve (570) to release the suction pressure such that the needle assembly (120) is separated apart from the skin.

4. The injection method of claim 3, wherein the third step (S3) selects among a continuous mode and a dose mode, wherein
    in the continuous mode, in accordance with continuous switching on of the foot switch (900), the motor of the injector (100) repeats operating on and off according to preset drug injection intervals such that drug injection continues for a predetermined time period, and
    in the dose mode, in accordance with the switching on of the foot switch (900), the motor of the injector (100) is operated one time according to the preset drug injection intervals such that drug is injected every time the foot switch (900) is operated.

5. The injection method of claim 3, wherein the first step (S1) comprises additionally setting on/off interval of the suction motor.

6. The injection method of claim 3, prior to the first step (S1), further comprising a step of setting a length of exposure of the needles (121) according to a depth of insertion into the skin.

7. The injection method of claim 3, wherein a liquid sucked in through the needles by the suction pressure of the suction motor (580) is discharged through the drain pipe (D) via the first suction pipe (541) and the four-directional connector (550).

8. The injection apparatus of claim 1, comprising a drain pipe (D) connected to the suction motor (580) and opened in accordance with an operation of the solenoid valve (570) to discharge a liquid sucked into the air hose (520).

9. An injection method using the injection apparatus as set forth in claim 8, the injection method comprising:
    a first step (S1) of setting one or more of drug injection mode, suction pressure, and a dosage of drug injection;

a second step (S2) of bringing the front end of the needle assembly (120) of the injector (100) into contact with the skin such that the skin blocks the front end of the needle, suction pressure is generated through the first suction pipe (541) and vacuum suction pressure is generated at the needle assembly (120) in contact with the skin;

a third step (S3) of comparing the vacuum suction pressure sensed at the second step (S2) with the preset suction pressure value to determine whether or not the needles (121) are inserted into the skin;

a fourth step (S4) of driving the motor of the injector (100) and performing treatment of injecting the drug through the needle (121); and a fifth step (S5) of stopping the suction motor (580) upon completion of the drug injection, and opening the solenoid valve (570) to release the vacuum suction pressure such that the needle assembly (120) is separated apart from the skin.

10. An injection method using the injection apparatus as set forth in claim 1, the injection method comprising:

a first step (S1) of setting one or more of drug injection mode, suction pressure, and a dosage of drug injection;

a second step (S2) of bringing the front rim of the needle assembly (120) of the injector (100) into contact with the skin such that the skin blocks the front rim of the needle assembly (120), the suction pressure is generated through the suction motor and the first suction pipe (541) and the vacuum suction pressure is generated at the needle assembly (120) in contact with the skin;

a third step (S3) of comparing the vacuum suction pressure sensed at the second step (S2) with the preset suction pressure value to determine whether or not the needles (121) are inserted into the skin;

a fourth step (S4) of driving the motor of the injector (100) and performing treatment of injecting the drug through the needles (121); and a fifth step (S5) of stopping the suction motor (580) upon completion of the drug injection, and opening the solenoid valve (570) to release the vacuum suction pressure such that the needle assembly (120) is separated apart from the skin.

11. The injection method of claim 10, wherein the first step (S1) comprises additionally setting on/off interval of the suction motor.

12. The injection method of claim 10, prior to the first step (S1), further comprising a step of setting a length of exposure of the needles (121) according to a depth of insertion into the skin.

13. The injection method of claim 10, wherein the fifth step (S5) comprises steps of:

releasing the suction pressure by turning off the suction motor (580); and opening the solenoid valve (570), wherein the opening of the solenoid valve (570) allows external air to be introduced into the first suction pipe (541) and the air hose (520), and to the injector (100), thus releasing the vacuum suction pressure and allowing the needle assembly (120) to be separated apart from the skin.

14. The injection method of claim 10, wherein a liquid sucked in through the needles by the suction pressure of the suction motor (580) is discharged through the drain pipe (D) via the first suction pipe (541) and the four-directional connector (550).

15. The injection apparatus of claim 1, wherein the main body includes a holder configured to receive the front rim of the needle assembly.

* * * * *